United States Patent [19]

Mager et al.

[11] 3,937,820

[45] Feb. 10, 1976

[54] INSULIN COMPOSITION PROVIDING ALTERNATIVES TO IMMUNOLOGICAL RESISTANCE

[75] Inventors: Adolf Mager, Niedernhausen; Hans-Hermann Schöne, Bad Soden, Taunus; Rolf Geiger, Frankfurt am Main; Franz Enzmann, Kelkheim, Taunus, all of Germany

[73] Assignee: Hoechst Aktiengesellschaft, Frankfurt am Main, Germany

[22] Filed: Nov. 14, 1973

[21] Appl. No.: 415,635

[30] Foreign Application Priority Data
Nov. 16, 1972 Germany.......................... 2256215

[52] U.S. Cl. ............................................. 424/178
[51] Int. Cl.$^2$................. A61K 37/26; C07C 103/52

[58] Field of Search.................. 260/112.7; 424/178

[56] References Cited
UNITED STATES PATENTS

| | | | |
|---|---|---|---|
| 3,364,116 | 1/1968 | Bodansky et al. .................. | 424/178 |
| 3,801,564 | 4/1974 | Geiger ............................. | 260/112.7 |

*Primary Examiner*—Lewis Gotts
*Assistant Examiner*—Reginald J. Suyat
*Attorney, Agent, or Firm*—Curtis, Morris & Safford

[57] ABSTRACT

A novel insulin composition of improved stability and compatibility comprising in an aqueous suspension crystallized insulin and amorphous des-phenylalanine$^{B1}$ insulin of the same species, and a method for its manufacture.

4 Claims, No Drawings

INSULIN COMPOSITION PROVIDING ALTERNATIVES TO IMMUNOLOGICAL RESISTANCE

The present invention relates to a novel pharmacological insulin composition having antidiabetic activity, and to a method for preparing it.

Up to the present, two methods have been employed for preparing insulin compositions having a depot effect: the one is to add to the insulin, in addition to zinc ions, retarding agents, such as bis-(4-amino-quinaldine-6)-N,N'-urea hydrochloride, globine or protamine, the other one is to use suspensions of crystallized or amorphous insulin.

The onset of activity of insulin obtained from crystal suspensions is slow and its effect continues, in many cases, for too long a time, whilst the effect caused by a suspension of amorphous insulin sets in immediately but wears off too rapidly.

Therefore, crystallized and amorphous insulins have also been combined to assure a more favorable time-effect ratio.

With such a combination, however, one has to make sure that amorphous insulin is not converted into crystallized insulin during the time of storage. Such a conversion has hitherto been prevented by using insulins of different species, for example crystallized bovine insulin and amorphous porcine insulin.

Such a combination has, however, the disadvantage of causing the formation of antibodies against the two species. Some years ago, mono-species insulins were used for the first time, thus assuring, when resistance to insulin occurs for immunological reasons, that use can be made of a different insulin which had not yet been administered, for example porcine insulin instead of bovine insulin. This possibility is, however, excluded when combinations of insulins of different species are used.

It has now been found that amorphous des-phenyl-alanine$^{B1}$ insulin and insulin having complete insulin crystals of the same species can be mixed to yield a stable combination without risking a conversion of amorphous des-phenyl-alanine$^{B1}$ insulin (des-Phe$^{B1}$ insulin) into a crystallized one. Even the presence of zinc ions does not cause any conversion.

Since, except for missing phenyl-alanine, des-phenyl-alanine$^{B1}$ insulin has the same immunogenic groupings as the corresponding complete insulin, the two insulins represent a two-phase (crystallized/amorphous) stable system which shows the immunological properties of a mono-species insulin.

Hence, the present invention provides an insulin composition containing, in addition to crystallized insulin, amorphous des-phenyl-alanine$^{B1}$ insulin of the same species in an aqueous suspension.

The pH-value of this suspension is advantageously adjusted to about 6.8 – 7.6, preferably to 7.0 – 7.4, and the suspension contains up to 340γ/100 I.U. of zinc ions.

The insulin crystals in the suspension advantageously have a uniform size of from 15 to 34 microns. The crystal suspension may contain, in addition to the zinc ions advantageously present in a concentration of 200γ/I.U. corresponding to 80 mg/ml of Zn, salts such as sodium acetate, advantageously in a concentration of 0.1 to 0.2%, or sodium chloride, advantageously in a concentration of 0.5 to 1 %, and/or preservatives, such as 4-hydroxy-benzoic acid methyl ester, advantageously in a concentration of about 0.1 %.

The composition of the insulin preparation may be varied within certain limits. The ratio of crystallized insulin to amorphous des-Phe$^{B1}$ insulin is responsible for the time-effect ratio and may range from about 60 : 40 to 80 : 20, preferably from 70 : 30 to 75 : 25. The overall insulin content of the composition is advantageously from 40 to 80 I.U./ml.

This invention moreover provides a method for making the aforementioned composition, which comprises mixing a suspension of insulin crystals with a suspension of amorphous des-phenyl-alanine$^{B1}$ insulin of the same species.

Des-Phe$^{B1}$ insulin has already been disclosed in the art but its property of forming stable two-phase systems with complete insulins of the same species has not been recognized as yet.

The composition according to the invention has a long-lasting insulin depot effect. Even after having been stored for one year at 25°C, it has not changed as far as its physical condition and its biological activity are concerned.

The composition is used as depot insulin for the treatment of diabetes mellitus. It is especially suitable for being administered to patients for the first time in order to prevent antibodies from being formed against several insulin species.

The following Examples illustrate the invention, the parts and percentages being by weight unless stated otherwise.

EXAMPLE 1.

A. Preparation of a zinc insulin crystal suspension

16 Grams of pure crystallized insulin having a minimum activity of 25 I.U./mg, calculated on dry substance, were dissolved in 750 ml of 0.02N hydrochloric acid containing 0.013 % of zinc ions in the form of zinc chloride. 250 ml of a solution containing 0.95 % of glacial acetic acid and 2.8 % of sodium chloride was added to this insulin solution. The clear mixture was then sterilized by sterile filtration over a membrane layer. Subsequently, sterile 4N sodium hydroxide was added to the sterile-filtered solution in such an amount that its pH-value ranged from 5.4 to 5.6. The amorphous insulin suspension obtained was stirred for a short time at room temperature under sterile conditions and then placed in a fridge at +4° to +7°C to initiate crystallization.

After a maximum storage time of 36 to 40 hours, rhombohedral crystals of uniform shape and size of from 18 to 30 microns were obtained. The crystals were centrifuged off at low speed in sterile beakers, whereupon small amorphous portions, if any, were separated. The centrifuged crystals were then again suspended in 1 l of a sterile buffered neutral insulin dilution solution (composed as in Table 1) (stock suspension).

TABLE 1

Composition of the insulin dilution solution:
10 liters of solution contained
10 g of Solbrol M (p-hydroxy-benzoic acid methyl ester) = 0.1 %
14 g of sodium acetate + 3 H$_2$O = 0.14 % = 0.01 mol
75 g of sodium chloride = 0.75 %
1.66 g of zinc chloride (ZnCL$_2$) = 80Γ of Zn$^{++}$/ml and sodium hydroxide up to pH 7.4, the whole being filtered under sterile conditions.

Determination of the insulin crystal content in the stock suspension

For determining the insulin crystal content in the stock suspension, 4 times 1 ml (full pipette) was taken from the crystal suspension after intimate mixing by means of a magnetic stirrer, and the content of insulin was determined according to the following methods:
1. Gravimetrical determination upon drying, using acetone and ether and weighing.
2. Spectrophotometrical determination of the ultraviolet band at 280 m$\mu$ upon dissolution of the crystals.
3. Determination of the nitrogen content.

Preparation of the depot component containing 40 I.U./ml

Depending on the insulin content determined in the stock suspension, the sterile dilute solution was then standardized by further dilution to reach the desired insulin content of 40 I.U./ml. Maximum yield: 10 liters.

B. Preparation of the amorphous component of des-phenyl-alanine$^{B1}$ insulin 6.304 g of des-Phe-alanine$^{B1}$ insulin were dissolved in 3.5 l of a solution liquid of the composition indicated in Table 2.

TABLE 2

Composition of the des-Phe$^{B1}$-solution liquid:
5 Liters of solution contained
5 g of Solbrol M (p-hydroxybenzoic acid methyl ester) =0.1 %
2.85 ml of glacial acetic acid containing about 0.14 % of Na-acetate + 3 H$_2$O
37.5 g of sodium chloride = 0.75 %
830 mg of zinc chloride (anhydrous) = 80 $\Gamma$ of Zn$^{++}$/ml
2.6 ml of 4N hydrochloric acid.

The clear solution of des-Phe$^{B1}$ insulin was then sterilized by means of a membrane filter and diluted to a volume of 3.9 l by adding 400 ml of a solution liquid which, after filtration of the insulin, had been passed through the same sterile filter. By addition of 4N sterile sodium hydroxide solution of pH is adjusted to 7.4 (consumption 13.6 ml). By further dilution with 34 ml of a sterile neutral insulin dilution solution, a final volume of 3.948 l was reached and thus standardized to an insulin content of 40 I.U./ml, based on an activity of the des-Phe$^{B1}$ starting insulin of 25 I.U./mg.

C. Preparation of a depot composition ready for being filled into ampoules

The crystal-containing depot component preapred according to A was mixed with the component prepared according to B, containing amorphous des-Phe$^{B1}$ insulin, at a volumetric ratio of 70 : 30, to yield a composition containing 28 I.U. of a crystallized component and 12 I.U. of an amorphous component, both making up 40 I.U. per ml. The suspension was filled under sterile conditions into bottles each containing 10 ml.

EXAMPLE 2

60 Parts of the component prepared according to A were mixed with 40 parts of the component prepared according to B, whereupon a composition was obtained containing 24 I.U. of a crystallized component and 16 I.U. of an amorphous component, both making up 40 I.U. per ml. The suspension was filled under sterile conditions in to bottles of 10 ml each.

EXAMPLE 3

75 Parts of the component prepared according to A were mixed with 25 parts of the component according to B to yield a composition containing 30 I.U. of the crystallized component and 10 I.U. of the amorphous component, together making up 40 I.U. of insulin per ml. The suspension was filled under sterile conditions into bottles of 10 ml each.

EXAMPLE 4

80 Parts of the component prepared according to A were mixed with 20 parts of the component prepared according to B to yield a composition containing 32 I.U. of the crystallized component and 8 I.U. of the amorphous component, both making up 40 I.U. of insulin per ml. The suspension was filled under sterile conditions into bottles of 10 ml each.

What is claimed is:
1. An insulin composition for providing an alternative to an immunological resistance to insulin of different mixed species of insulin which comprises, in an aqueous suspension, a crystallized insulin and an amorphous des-phenyl-alanine$^{B1}$ insulin of the same species, having a pH value in the range of from 6.8 to 7.6, containing zinc ions in an amount of up to 340$\gamma$/100 I.U., wherein the insulin crystals have a uniform size of from 15 to 35 microns; wherein the ratio of crystallized insulin to amorphous des-phenyl-alanine$^{B1}$ insulin ranges from 60 : 40 to 80 : 20; and wherein the insulin content is from 40 to 80 I.U. per ml.
2. An insulin composition as claimed in claim 1, wherein the two insulin components are porcine.
3. An insulin composition as claimed in claim 1, wherein the two insulin components are bovine.
4. A process for the manufacture of an aqueous insulin composition as claimed in claim 1, which comprises mixing a suspension of insulin crystals with a suspension of amorphous desphenyl-alanine$^{B1}$ insulin of the same species.

* * * * *